United States Patent
Fischer

[11] 3,938,984
[45] Feb. 17, 1976

[54] HERBICIDE
[75] Inventor: Adolf Fischer, Mutterstadt, Germany
[73] Assignee: BASF Aktiengesellschaft, Ludwigshafen (Rhine), Germany
[22] Filed: May 23, 1974
[21] Appl. No.: 472,654

Related U.S. Application Data
[62] Division of Ser. No. 348,085, April 4, 1973.

[30] Foreign Application Priority Data
Apr. 13, 1972 Germany............................ 2217698

[52] U.S. Cl..................................... 71/88; 71/111
[51] Int. Cl.²........................................ A01N 9/28
[58] Field of Search................................ 71/88, 111

[56] References Cited
UNITED STATES PATENTS
3,551,477  12/1970  Koenig et al..................... 71/111 X
3,689,507  9/1972  Gates et al......................... 71/88 X
3,692,820  9/1972  Boroschewski................... 71/111 X

*Primary Examiner*—Lewis Gotts
*Assistant Examiner*—Catherine L. Mills
*Attorney, Agent, or Firm*—Johnston, Keil, Thompson & Shurtleff

[57] ABSTRACT

New and valuable herbicide mixtures of 2-ethoxy-2,3-dihydro-3,3-dimethyl-5-benzofuranylmethane sulfonate and carbamates of the formula

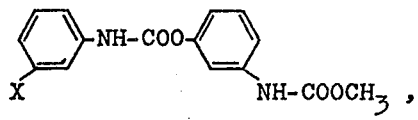

where X denotes hydrogen or lower alkyl.

8 Claims, No Drawings

HERBICIDE

RELATED APPLICATION

This application is a division of my copending application Ser. No. 348,085, filed Apr. 4, 1973, the disclosure of which is incorporated herein by reference.

The present invention relates to herbicide mixtures of 2-ethoxy-2,3-dihydro-3,3-dimethyl-5-benzofuranylmethane sulfonate and carbamates having the above formula.

It is known to use methane sulfonates and carbamates for controlling broadleaved and grassy weeds. However, their action is poor.

I have now found that a composition of
a. a compound of the formula

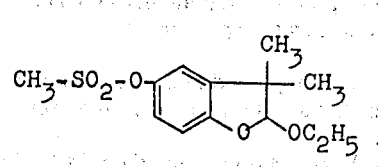

and
b. a compound of the formula

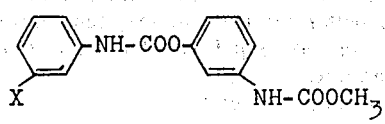

where X denotes hydrogen or lower alkyl of a maximum of 3 carbon atoms, has a good herbicidal action.

The active ingredients may be mixed in any ratio, it is however preferred to employ a ratio (by weight) of $a:b$ of from 5:1 to 1:5, preferably 3:1 to 1:3.

The agents according to the invention may be used as solutions, emulsions, suspensions, oil dispersions, granules or dusts. The form of application depends entirely on the purpose for which the agents are being used; in any case it should ensure a fine distribution of the active ingredient.

For the preparation of solutions to be sprayed direct, mineral oil fractions of medium to high boiling point, such as kerosene or diesel oil, further coal-tar oils and oils of vegetable or mineral origin, and cyclic hydrocarbons such as tetrahydronaphthalene and alkylated naphthalenes are suitable.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g., polyethylene oxide adducts. Concentrates which are suitable for dilution with water may be prepared from active ingredient, wetting agent, adherent, emulsifying or dispersing agent and possibly solvent. Oils of various types may be added to ready-to-use spray liquors.

Dusts may be prepared by mixing or grinding the active ingredients with a solid carrier, e.g., kieselguhr, talc, clay or fertilizers.

Granules may be prepared by bonding the active ingredients to solid carriers.

Directly sprayable dispersions may also be prepared with oils.

The new compounds may be mixed with fertilizers, insecticides, fungicides and other herbicides.

The new herbicides may be applied either pre- or post-emergence, and are particularly suited for controlling dicotyledonous seed weeds and monocotyledonous seed grasses in crops such as beet, spinach, potatoes, peas, beans and groundnuts.

EXAMPLE 1

The plants beet (*Beta vulgaris*), common lambsquarters (*Chenopodium album*), chamomile (*Matricaria chamomilla*), wild mustard (*Sinapis arvensis*), slender foxtail (*Alopecurus myosuroides*), and annual bluegrass (*Poa annua*) were treated at a growth height of 3 to 13 cm with the following amounts of the following active ingredients and compositions thereof, each active ingredient and each composition being emulsified or dispersed in 500 liters of water per hectare:

I. 2-ethoxy-2,3-dihydro--3,3-dimethyl-5-benzofuranylmethane sulfonate, 0.5, 1, 1.5, 2 and 3 kg/hectare;
II. 3-methoxycarbonylaminophenyl-N-(3'-methylphenyl)-carbamate, 1 and 2 kg per hectare;
III. 1-phenyl-4-amino-5-chloropyridazone-(6), 2 and 3 kg per hectare;
IV. 1-phenyl-4-($\alpha$-hydroxy-$\beta,\beta,\beta$-trichloroethyl)-amino-5- bromopyridazone-(6), 1.5 and 2 kg/hectare;
V. 1-($\alpha,\alpha$-dimethyl-$\beta$-acetoxypropionyl)-3-cyclohexyl-5,6-trimethylene uracil, 0.5 and 2 kg/hectare;
VI. 3-cyclohexyl-5,6-trimethylene uracil, 1 and 2 kg/hectare;
I + II: 1 + 1 kg/hectare;
I + III: 1 + 2 kg/hectare;
I + IV: 0.5 + 1.5 kg/hectare;
I + V: 1.5 + 0.5 kg/hectare;
I + VI: 1 + 1 kg/hectare.

After 2 to 3 weeks it was ascertained that the compositions had a better herbicidal action that their individual components, combined with good crop plant compatibility.

The results are given below:

| Active ingredient | I | | | | | II | | III | | IV | |
| --- | --- | --- | --- | --- | --- | --- | --- | --- | --- | --- | --- |
| kg/ha | 0.5 | 1 | 1.5 | 2 | 3 | 1 | 2 | 2 | 3 | 1.5 | 2 |
| Beta vulgaris | 0 | 0 | 5 | 20 | 30 | 0 | 20 | 0 | 0 | 0 | 0 |
| Chenopodium album | 10 | 20 | 35 | 50 | 70 | 80 | 100 | 65 | 90 | 60 | 85 |
| Matricaria chamomilla | 20 | 30 | 50 | 70 | 90 | 35 | 80 | 60 | 90 | 65 | 90 |
| Sinapis arvensis | 10 | 20 | 40 | 60 | 90 | 75 | 100 | 50 | 85 | 60 | 80 |
| Alopecurus myosuroides | 30 | 50 | 60 | 100 | 100 | 10 | 15 | 40 | 80 | 40 | 50 |
| Poa annua | 25 | 45 | 55 | 90 | 100 | 10 | 20 | 35 | 75 | 45 | 60 |

-continued

| Active ingredient kg/ha | V 0.5 | VI 1 | 2 | I+II 1+1 | I+III 1+2 | I+IV 0.5+1.5 | I+V 1.5+0.5 | I+VI 1+1 |
|---|---|---|---|---|---|---|---|---|
| | | 2 | | | | | | |
| Beta vulgaris | 0 | 20 | 5 | 25 | 0 | 0 | 0 | 5 | 5 |
| Chenopodium album | 30 | 100 | 50 | 100 | 100 | 100 | 100 | 95 | 95 |
| Matricaria chamomilla | 35 | 95 | 40 | 90 | 100 | 100 | 95 | 100 | 100 |
| Sinapis arvensis | 40 | 100 | 65 | 100 | 100 | 100 | 100 | 100 | 100 |
| Alopecurus myosuroides | 25 | 95 | 45 | 90 | 90 | 100 | 95 | 100 | 100 |
| Poa annua | 30 | 100 | 45 | 90 | 85 | 95 | 90 | 100 | 100 |

0 = no damage
100 = complete destruction

EXAMPLE 2

In the greenhouse, various plants were treated at a growth height of 3 to 11 cm with the following amounts of the following active ingredients and compositions thereof as dusts:

I.  2-ethoxy-2,3-dihydro-3,3-dimethyl-5-benzofuranylmethane sulfonate, 0.1, 1.0 and 1.2 kg/ha;
II. 3-methoxycarbonylaminophenyl-N-(3'-methylphenyl)-carbamate, 0.1, 1.0 and 1.2 kg/ha;
III. 1-phenyl-4-amino-5-chloropyridazone-(6), 0.1, 1.0 and 1.2 kg/ha;
I+II+III: 0.1+0.1+1.0, 0.1+1.0+0.1 and 1.0+0.1+0.1 kg/ha.

After 2 to 3 weeks it was ascertained that the compositions had a better herbicidal action than their individual components combined with the same good crop plant compatibility.
The results are given below:

EXAMPLE 3

In the greenhouse various plants were treated at a growth height of 4 to 12 cm with the following amounts of the following active ingredients and compositions thereof as concentrated spray liquors;

I.  2-ethoxy-2,3-dihydro-3,3-dimethyl-5-benzofuranylmethane sulfonate, 0.1, 0.5, 0.9 and 1.0 kg/ha;
II. 3-methoxycarbonylaminophenyl-N-(3'-methylphenyl)-carbamate, 0.1, 0.5, 0.9 and 1.0 kg/ha;
I + II 0.1+0.9, 0.9+0.1 and 0.5+0.5 kg/ha.

After 2 to 3 weeks it was ascertained that the compositions had a better herbicidal action than their individual components, combined with the same good crop plant compatibility.
The results are given below:

| Active ingredient kg/ha | I 0.1 | 1.0 | 1.2 | II 0.1 | 1.0 | 1.2 | III 0.1 | 1.0 | 1.2 |
|---|---|---|---|---|---|---|---|---|---|
| Crop plants: | | | | | | | | | |
| Beta vulgaris | 0 | 0 | 0 | 0 | 0 | 0 | 0 | 0 | 0 |
| Unwanted plants: | | | | | | | | | |
| Avena fatua | 8 | 50 | 56 | 2 | 20 | 23 | 1 | 10 | 11 |
| Bromus tectorum | 12 | 55 | 57 | 2 | 15 | 18 | 0 | 20 | 21 |
| Matricaria chamomilla | 3 | 30 | 33 | 5 | 35 | 39 | 5 | 40 | 44 |
| Setaria faberii | 8 | 55 | 58 | 3 | 20 | 23 | 1 | 20 | 24 |
| Sinapis arvensis | 1 | 20 | 26 | 8 | 75 | 81 | 13 | 35 | 39 |

0 = no damage
100 = complete destruction

| Active ingredients kg/ha | I 0.1 | 0.5 | 0.9 | 1.0 | II 0.1 | 0.5 | 0.9 | 1.0 | I+II 0.1+0.9 | 0.9+0.1 | 0.5+0.5 |
|---|---|---|---|---|---|---|---|---|---|---|---|
| Crop plants: | | | | | | | | | | | |
| Beta vulgaris | 0 | 0 | 0 | 0 | 0 | 0 | 0 | 0 | 0 | 0 | 0 |
| Unwanted plants: | | | | | | | | | | | |
| Avena fatua | 8 | 25 | 48 | 50 | 2 | 10 | 19 | 20 | 80 | 90 | 70 |
| Bromus tectorum | 12 | 30 | 50 | 55 | 2 | 8 | 14 | 15 | 85 | 95 | 80 |
| Matricaria chamomilla | 3 | 20 | 28 | 30 | 5 | 18 | 33 | 35 | 70 | 60 | 68 |
| Setaria berii | 8 | 35 | 52 | 55 | 3 | 10 | 19 | 20 | 88 | 96 | 86 |
| Sinapis arvensis | 1 | 10 | 18 | 20 | 8 | 35 | 72 | 75 | 100 | 80 | 80 |

O = no damage
100 = complete destruction

| Active ingredient kg/ha | I + II + III 0.1+0.1+1.0 | I + II + III 0.1+1.0+0.1 | I + II + III 1.0+0.1+0.1 |
|---|---|---|---|
| Crop plants: | | | |
| Beta vulgaris | 0 | 0 | 0 |
| Unwanted plants: | | | |
| Avena fatua | 78 | 80 | 90 |
| Bromus tectorum | 87 | 90 | 95 |
| Matricaria chamomilla | 90 | 85 | 65 |
| Setaria faberii | 80 | 83 | 95 |
| Sinapis arvensis | 100 | 95 | 75 |

O = no damage
100 = complete destruction

I claim:
1. A herbicide composition containing a herbicidally effective amount of a mixture consisting essentially of
   a. a compound of the formula

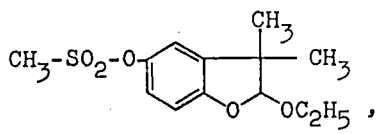

and
   b. a compound of the formula

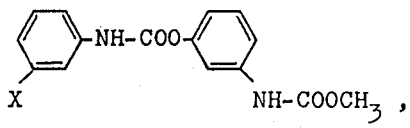

where X denotes hydrogen or lower alkyl of a maximum of 3 carbon atoms in a weight ratio of *a* to *b* in the range of 9:1 to 1:9.

2. A herbicide composition as claimed in claim 1 wherein X is hydrogen.

3. A herbicide composition as claimed in claim 1 wherein X is lower alkyl of a maximum of 3 carbon atoms.

4. A process for controlling the growth of unwanted plants in a host soil which comprises applying to the plants after emergence of said plants from the host soil a herbicide composition containing a herbicidally effective amount of a mixture consisting essentially of
   a. a compound of the formula

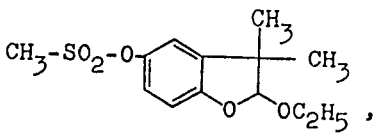

and
   b. a compound of the formula

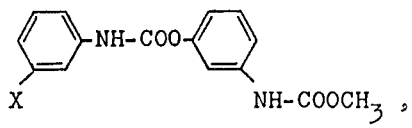

where X denotes hydrogen or lower alkyl of a maximum of 3 carbon atoms in a weight ratio of *a* to *b* in the range of 9:1 to 1:9.

5. A process as claimed in claim 4 wherein X is hydrogen.

6. A process as claimed in claim 4 wherein X is lower alkyl of a maximum of 3 carbon atoms.

7. A herbicide composition as claimed in claim 1 wherein X is methyl.

8. A process as claimed in claim 4 wherein X is methyl.

* * * * *